United States Patent
Yanagimoto et al.

(10) Patent No.: US 11,679,091 B2
(45) Date of Patent: Jun. 20, 2023

(54) LYMPHATIC CIRCULATION IMPROVING AGENTS

(71) Applicant: NIPPON SUISAN KAISHA, LTD., Tokyo (JP)

(72) Inventors: Kenichi Yanagimoto, Tokyo (JP); Li Han, Tokyo (JP); Bungo Shirouchi, Fukuoka (JP)

(73) Assignee: Nippon Suisan Kaisha, Ltd., Tokyo (JP)

( * ) Notice: Subject to any disclaimer, the term of this patent is extended or adjusted under 35 U.S.C. 154(b) by 303 days.

(21) Appl. No.: 16/968,321

(22) PCT Filed: Feb. 8, 2019

(86) PCT No.: PCT/JP2019/004588
§ 371 (c)(1),
(2) Date: Aug. 7, 2020

(87) PCT Pub. No.: WO2019/156210
PCT Pub. Date: Aug. 15, 2019

(65) Prior Publication Data
US 2021/0077447 A1    Mar. 18, 2021

(30) Foreign Application Priority Data
Feb. 9, 2018    (JP) .............................. JP2018-022378

(51) Int. Cl.
| | | |
|---|---|---|
| *A61K 31/202* | (2006.01) | |
| *A23L 33/12* | (2016.01) | |
| *A23L 33/00* | (2016.01) | |
| *A61P 7/10* | (2006.01) | |
| *A61K 31/232* | (2006.01) | |

(52) U.S. Cl.
CPC ............ *A61K 31/202* (2013.01); *A23L 33/12* (2016.08); *A23L 33/40* (2016.08); *A61K 31/232* (2013.01); *A61P 7/10* (2018.01); *A23V 2002/00* (2013.01)

(58) Field of Classification Search
CPC .................................................. A61K 31/202
See application file for complete search history.

(56) References Cited

U.S. PATENT DOCUMENTS

| | | |
|---|---|---|
| 4,607,052 A | 8/1986 | Mendy et al. |
| 2018/0153951 A1* | 6/2018 | Zhong ................... A61K 45/06 |

FOREIGN PATENT DOCUMENTS

| | | |
|---|---|---|
| JP | 63-154618 A | 6/1988 |
| JP | 2722229 B2 | 11/1997 |
| JP | 2001-226693 A | 8/2001 |
| WO | WO-88/09325 A1 | 12/1988 |
| WO | WO-89/02275 A1 | 3/1989 |
| WO | WO-90/04010 A1 | 4/1990 |
| WO | WO-2005/037848 A2 | 4/2005 |
| WO | WO-2015/050071 A1 | 4/2015 |
| WO | WO-2016/040570 A2 | 3/2016 |

OTHER PUBLICATIONS

Xu et al., Nutrition & Metabolism, 2015, 12:58/1-58/10.*
Brown et al., AIDS, 2010, 24(6): 811-7.*
Olza et al., Clinical Nutrition, 2010, 29(1): 31-37.*
Shimazawa et al., Brain Research, 2009, 1251: 269-275.*
International Search Report dated Apr. 2, 2019, in PCT/JP2019/004588.
Nankervis et al., "Effect of lipid vehicle on the intestinal lymphatic transport of isotretinoin in the rat," International Journal of Pharmaceutics, 1995, 119:173-181.
Turner et al., "Intestinal Lymph Flow and Lymphatic Transport of Protein During Fat Absorption," Quarterly Journal of Experimental Physiology, 1977, 62:175-180.
Supplementary European Search Report dated Oct. 6, 2021.
Biochemical Dictionary, 3rd Edition, Tokyo Kagaku Dojin Co., Ltd., 1998, p. 1330, "polyenoic fatty acid" with English translation.
Biochemical Dictionary, 3rd Edition, Tokyo Kagaku Dojin Co., Ltd., 1998, p. 877, "middle chain triacylglycerol," with English translation.
Igaku-Shoin Medical Dictionary, 1st edition, Igaku-Shoin Ltd., 2003, p. 1626, "medium chain triglyceride [MCT] [middle chain triacylglycerol]," with English translation.

* cited by examiner

*Primary Examiner* — Rei Tsang Shiao
(74) *Attorney, Agent, or Firm* — Foley & Lardner LLP

(57) ABSTRACT

The present invention provides a composition for improving lymphatic circulation, which contains a component selected from at least one highly unsaturated fatty acid, salt thereof, and ester thereof as an active ingredient. The present invention also provides a composition for improving lymphatic circulation, which contains as active ingredients a triglyceride comprising the at least one highly unsaturated fatty acid as a constituent fatty acid and a triglyceride comprising the at least one middle chain fatty acid as a constituent fatty acid. The present invention also provides a composition for improving lymphatic circulation, which contains as an active ingredient a triglyceride comprising the at least one highly unsaturated fatty acid and the at least one middle chain fatty acid as constituent fatty acids.

6 Claims, 2 Drawing Sheets

LYMPHATIC CIRCULATION IMPROVING AGENTS

CROSS-REFERENCE TO RELATED APPLICATIONS

This application is the U.S. National Stage of PCT/JP2019/004588, filed Feb. 8, 2019, which claims priority to JP 2018-022378, filed Feb. 9, 2018.

TECHNICAL FIELD

The present invention relates to a technology for improving lymphatic circulation

BACKGROUND ART

The lymphatic vascular system begins with lymphatic capillaries responsible for the absorption of the tissue fluid present in tissue spaces; the lymphatic capillaries lead to collecting lymphatic vessels, then to larger lymphatic trunks (including the thoracic duct) and are connected to veins at the venous angle (the site where the subclavian and internal jugular veins converge.) Hence, unlike the vascular system that composes a closed circulation system, the lymphatic vascular system is semicircular. Lymphatic circulation refers to the flow of lymph inside the lymphatic vascular system and is synonymous with lymph transport.

A disorder in lymphatic circulation (i.e., less efficient lymph flow) will cause a protein-rich body fluid to stay within intercellular spaces and this results in lymphedema. Immunity is lowered at the site of onset of lymphedema and bacterial or otherwise infection may sometimes even result from slight trauma to cause acute inflammations (cellulitis and lymphangitis.) In addition, lymphedema may develop from a treatment of breast cancer, uterus cancer, prostate cancer, etc. if it involves an excision of lymph nodes near the lesion and its manifestation will considerably lower the QOL of patients. Lymphedema, once manifested, is not easy to cure completely and once the chronic stage is reached where the subcutaneous tissue starts to change (the condition of a hardened skin surface is called elephantiasis), it is extremely difficult to reverse the symptom. This explains the need to perform appropriate self-care from the early stage.

Currently known therapies of lymphedema include daily life guidance (body weight reduction is recommended because fats will compress lymphatic vessels to render the lymph flow less efficient), skin care for preventing infections, exercise therapy under compression, manual lymph drainage, and so forth. On the other hand, compositions that can ameliorate lymphedema by the oral route have little been reported to date.

The lymphatic vascular system through which lymphocytes (immunocytes) circulate also plays an important role as a site of biological defense. At lymph nodes, antigens in lymph such as foreign materials (proteins) and bacteria are blocked and incorporated into macrophages, dendritic cells, and the like, so that the antigenic information is transmitted to the immune system. Therefore, improved lymphatic circulation is also considered to be important for enhancing immunological functions.

Highly unsaturated fatty acids contained in fish oils, such as eicosapentanoic acid (hereunder referred to as EPA) and docosahexaenoic acid (hereunder referred to as DHA) are known to have various physiological actions. For instance, EPA is known to have an efficacy in ameliorating dyslipidemia (hyperlipidemia) or the like such as hypertriglyceridemia. These highly unsaturated fatty acids are therefore used widely as pharmaceuticals, health foods, food ingredients and so forth.

For use as pharmaceuticals, ethyl esters of highly unsaturated fatty acids are common, and for use as health foods and the like, triglycerides as in purified fish oils are common.

Middle chain fatty acids are absorbed well, so there have been several reports on the idea of enhancing the absorption of highly unsaturated fatty acids by formulating a triglyceride that contains a highly unsaturated fatty acid(s) and a middle chain fatty acid(s).

Patent Document 1 discloses a composition suitable for parenteral administration that comprises a triglyceride that comprises 1-20% of $C_{20-22}$ fatty acids, 30-50% of $C_{14-18}$ fatty acids and 40-60% of $C_{6-12}$ fatty acids as constituent fatty acids and which can be used for treatment or prevention of arteriosclerosis and hyperlipidemia.

Patent Document 2 teaches that a triglyceride prepared by ester interchange between a fish oil and a middle chain fatty acid triglyceride is absorbed so quickly that it is suitable as a nutrient substitute that can be applied to patients and other subjects with lowered resistance against infection.

Patent Document 3 discloses an oil or fat composition having a blood lipid modulating function that is a triglyceride containing 5-55% of n-3 long chain polyunsaturated fatty acids and 2-40% of middle chain fatty acids.

Patent Documents 4-6, which are based on the finding that fatty acids attached to a triglyceride at 1- and 3-positions are not easily absorbed because they are resistant to decomposition by lipase, teach that a triglyceride having a highly unsaturated fatty acid attached at 2-position and middle chain fatty acids attached at 1- and 3-positions is suitable as an infusion solution or enteral nutrient that can be applied to patients with lowered absorption.

Patent Document 7 teaches that ingestion of a triglyceride comprising fatty acids derived from an EPA-containing fish oil and middle chain fatty acids as constituent fatty acids permits faster EPA absorption and can maintain high blood EPA levels, as compared with a mixture of a purified fish oil and a triglyceride comprising middle chain fatty acids as constituent fatty acids.

CITATION LIST

Patent Literature

Patent Document 1: JP S63-154618 A
Patent Document 2: Japanese Patent No. 2722229
Patent Document 3: JP 2001-226693 A
Patent Document 4: U.S. Pat. No. 4,607,052
Patent Document 5: WO 88/09325
Patent Document 6: WO 90/04010
Patent Document 7: WO 2015/050071

SUMMARY OF INVENTION

Technical Problem

An object of the present invention is to provide a means for alleviating various symptoms that accompany the stagnation of lymphatic circulation.

Solution to Problem

Using model rats for semi-permanent cannulation of thoracic duct lymph, the present inventors evaluated the lymph flow rate observed when the animals ingested various kinds of feed and found unexpectedly that the ingestion of feeds comprising highly unsaturated fatty acids increased the lymph flow rate. The present inventors also found that the increase of the lymph flow rate was more marked when the animals ingested triglycerides comprising a highly unsaturated fatty acid(s) and a middle chain fatty acid(s) as constituent fatty acids in one molecule.

Based on these findings, the present inventors continued their study to eventually accomplish the present invention.

Briefly, the present invention is as follows.

[1] A composition for improving lymphatic circulation, which contains a component selected from at least one highly unsaturated fatty acid, salt thereof, and ester thereof as an active ingredient.

[2] The composition as recited in [1], which further contains a component selected from at least one middle chain fatty acid, salt thereof, and ester thereof as an active ingredient.

[3] The composition as recited in [1] or [2], wherein the active ingredients are a triglyceride comprising the at least one highly unsaturated fatty acid as a constituent fatty acid and a triglyceride comprising the at least one middle chain fatty acid as a constituent fatty acid.

[4] The composition as recited in any one of [1]-[3], wherein the active ingredient is a triglyceride comprising the at least one highly unsaturated fatty acid and the at least one middle chain fatty acid as constituent fatty acids.

[5] The composition as recited in [3] or [4], wherein the at least one highly unsaturated fatty acid in the composition accounts for 10-70 wt % of constituent fatty acids and the at least one middle chain fatty acid in the composition accounts for 20-70 wt % of constituent fatty acids.

[6] The composition as recited in any one of [1]-[5], wherein each of the at least one highly unsaturated fatty acid is a fatty acid with a carbon number of 20 or more.

[7] The composition as recited in any one of [1]-[6], wherein the at least one highly unsaturated fatty acid is eicosapentaenoic acid or docosahexaenoic acid.

[8] The composition as recited in any one of [1]-[7], which is used for ameliorating edema, ameliorating excessive sensitivity to cold, ameliorating skin roughness, ameliorating skin dullness, reducing cellulites and body fat, mitigating stress, excreting wastes out of the body, or ameliorating disorders due to exercise.

[9] A food composition or a food additive for improving lymphatic circulation, which comprises the composition as recited in any one of [1]-[8].

[10] A method of producing a food composition or a food additive for improving lymphatic circulation, which comprises incorporating the composition as recited in any one of [1]-[8] in a food composition or food additive, thereby imparting a lymphatic circulation improving function to the food composition or food additive.

[10] A method of improving lymphatic circulation, which comprises allowing a subject to ingest an effective amount of a composition which contains a component selected from at least one highly unsaturated fatty acid, salt thereof, and ester thereof as an active ingredient.

[11] The method as recited in [10], wherein the composition further contains a component selected from at least one middle chain fatty acid, salt thereof, and ester thereof as an active ingredient.

[12] The method as recited in [10] or [11], wherein the active ingredients are a triglyceride comprising the at least one highly unsaturated fatty acid as a constituent fatty acid and a triglyceride comprising the at least one middle chain fatty acid as a constituent fatty acid.

[13] The method as recited in any one of [10]-[12], wherein the active ingredient is a triglyceride comprising the at least one highly unsaturated fatty acid and the at least one middle chain fatty acid as constituent fatty acids.

[14] The method as recited in [12] or [13], wherein the at least one highly unsaturated fatty acid in the composition accounts for 10-70 wt % of constituent fatty acids and the at least one middle chain fatty acid in the composition accounts for 20-70 wt % of constituent fatty acids.

[15] The method as recited in any one of [10]-[14], wherein each of the at least one highly unsaturated fatty acid is a fatty acid with a carbon number of 20 or more.

[16] The method as recited in any one of [10]-[15], wherein the at least one highly unsaturated fatty acid is eicosapentaenoic acid or docosahexaenoic acid.

[17] The method as recited in any one of [10]-[16], which is for ameliorating edema, ameliorating excessive sensitivity to cold, ameliorating skin roughness, ameliorating skin dullness, reducing cellulites and body fat, mitigating stress, excreting wastes out of the body, or ameliorating disorders due to exercise.

[18] The method as recited in any one of [10]-[17], wherein the composition is in the form of a food composition or a food additive.

[19] A composition for use in improvement of lymphatic circulation, which contains a component selected from at least one highly unsaturated fatty acid, salt thereof, and ester thereof as an active ingredient.

[20] The composition as recited in [19], which further contains a component selected from at least one middle chain fatty acid, salt thereof, and ester thereof as an active ingredient.

[21] The composition as recited in [19] or [20], wherein the active ingredients are a triglyceride comprising the at least one highly unsaturated fatty acid as a constituent fatty acid and a triglyceride comprising the at least one middle chain fatty acid as a constituent fatty acid.

[22] The composition as recited in any one of [19]-[21], wherein the active ingredient is a triglyceride comprising the at least one highly unsaturated fatty acid and the at least one middle chain fatty acid as constituent fatty acids.

[23] The composition as recited in [21] or [22], wherein the at least one highly unsaturated fatty acid in the composition accounts for 10-70 wt % of constituent fatty acids and the at least one middle chain fatty acid in the composition accounts for 20-70 wt % of constituent fatty acids.

[24] The composition as recited in any one of [19]-[23], wherein each of the at least one highly unsaturated fatty acid is a fatty acid with a carbon number of 20 or more.

[25] The composition as recited in any one of [19]-[24], wherein the at least one highly unsaturated fatty acid is eicosapentaenoic acid or docosahexaenoic acid.

[26] The composition as recited in any one of [19]-[25], which is for use in ameliorating edema, ameliorating excessive sensitivity to cold, ameliorating skin roughness, ameliorating skin dullness, reducing cellulites and body fat, mitigating stress, excreting wastes out of the body, or ameliorating disorders due to exercise.

[27] The composition as recited in any one of [19]-[26], which is in the form of a food composition or a food additive.

[28] Use of a composition containing a component selected from at least one highly unsaturated fatty acid, salt thereof, and ester thereof as an active ingredient, for manufacturing a composition for improving lymphatic circulation.

[29] Use as recited in [28], wherein the composition further contains a component selected from at least one middle chain fatty acid, salt thereof, and ester thereof as an active ingredient.

[30] Use as recited in [28] or [29], wherein the active ingredients are a triglyceride comprising the at least one highly unsaturated fatty acid as a constituent fatty acid and a triglyceride comprising the at least one middle chain fatty acid as a constituent fatty acid.

[31] Use as recited in any one of [18]-[30], wherein the active ingredient is a triglyceride comprising the at least one highly unsaturated fatty acid and the at least one middle chain fatty acid as constituent fatty acids.

[32] Use as recited in [30] or [31], wherein the at least one highly unsaturated fatty acid in the composition accounts for 10-70 wt % of constituent fatty acids and the at least one middle chain fatty acid in the composition accounts for 20-70 wt % of constituent fatty acids.

[33] Use as recited in any one of [28]-[32], wherein each of the at least one highly unsaturated fatty acid is a fatty acid with a carbon number of 20 or more.

[34] Use as recited in any one of [28]-[33], wherein the at least one highly unsaturated fatty acid is eicosapentaenoic acid or docosahexaenoic acid.

[35] Use as recited in any one of [28]-[34], wherein the composition for improving lymphatic circulation is used for ameliorating edema, ameliorating excessive sensitivity to cold, ameliorating skin roughness, ameliorating skin dullness, reducing cellulites and body fat, mitigating stress, excreting wastes out of the body, or ameliorating disorders due to exercise.

[36] Use as recited in any one of [28]-[35], wherein the composition for improving lymphatic circulation is in the form of a food composition or a food additive.

Advantageous Effects of Invention

Lymphatic circulation can be improved by orally ingesting the composition of the present invention.

DESCRIPTION OF EMBODIMENTS

Figure 1:
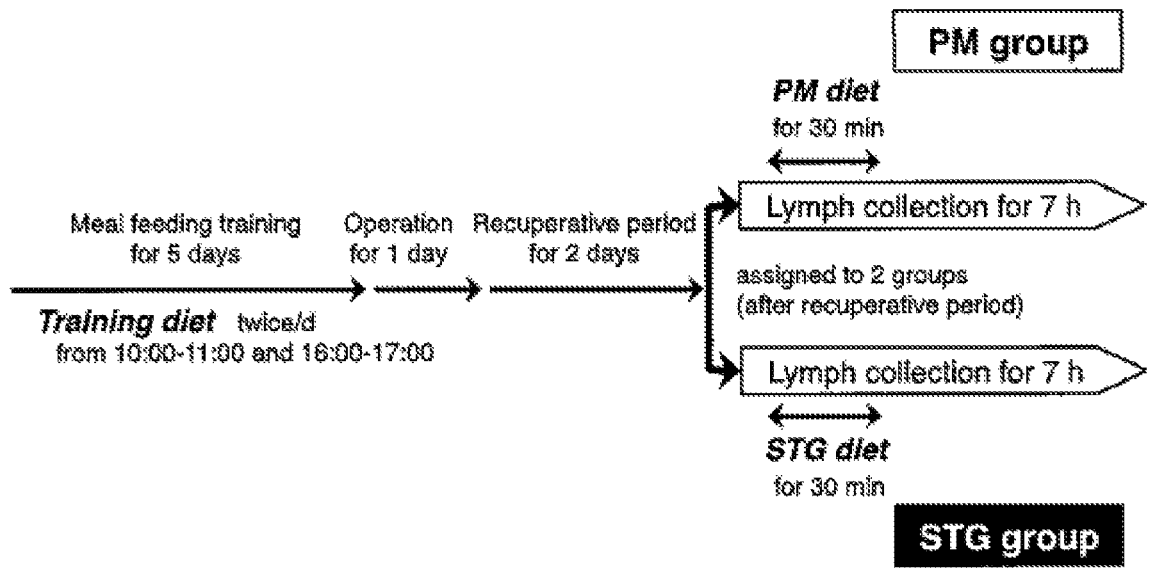
FIG. 1 is a diagram showing the schedule of feeding laboratory animals in the Examples. STG: eicosapentaenoic acid (EPA)/middle chain fatty acid (MCFA) structured lipid; PM: a mixed oil or fat as prepared by physically mixing an EPA containing fish oil with MCFA triacylglycerol (MCT) and then adjusting the mixture to become identical with STG in terms of fatty acid composition.

On the pages that follow, the present invention will be explained more specifically.
The following abbreviations are sometimes used herein:
EPA for eicosapentaenoic acid;
DHA for docosahexaenoic acid;
MCFA for middle chain fatty acid;
MCT for a triglyceride having only middle chain fatty acids as constituent fatty acids;
STG for a structured triglyceride, a structured triacylglycerol, or a structured lipid.

The present invention provides a composition for improving lymphatic circulation, which contains a component selected from at least one highly unsaturated fatty acid, salt thereof, and ester thereof as an active ingredient (this composition is hereunder sometimes referred to as the composition of the present invention).

As used herein, the term "improving lymphatic circulation" refers to an improvement in the flow of lymph in the lymphatic vascular system. Improvement of lymphatic circulation can be evaluated using the lymph flow rate in laboratory animals as an index. The lymph flow rate here referred to is affected by constraint, anesthesia and other events, so a semi-permanent method for cannulation of thoracic duct lymph is used because it allows meals to be ingested and lymph collected over time, without need for anesthesia and constraint (Lipids (2011) 46: 789-793). Specifically, based on the method described in Example, surgery for semi-permanent cannulation of thoracic duct lymph was performed on laboratory animals and the lymph flow rate measured in the following manner. First, a medical tube filled with heparin in physiological saline was inserted into the thoracic duct of each rat, fixed and sutured to the endothelium, and thereafter fixed to the head by a subcutaneous route. After the surgery, a 2-day recuperative period was provided and at the $3^{rd}$ post-operation day, the animals were divided into a test substance group and a control group; the test substance group was fed a test substance containing diet for 30 minutes whereas the control group was fed a test substance free diet for 30 minutes. Lymph was collected for 20 minutes before feeding and for one or more hours after the start of feeding. The lymph flow rate per hour (mL/h) was calculated from the collected lymph. In the case where the lymph flow rate per hour (mL/h) or cumulative lymph flow rate (mL) in the test substance group increased significantly as compared with the control group, the test substance of interest is evaluated as having a lymph circulation improving effect. The composition of the present invention is particularly high in the effect for increasing the lymph flow rate (mL/h) from ingestion until the passage of an hour.

As used herein, the term "at least one highly unsaturated fatty acid" refers to a fatty acid(s) with a carbon number of 18 or more and a double bond number of 3 or more, for example, a fatty acid(s) with a carbon number of 20 or more and a double bond number of 3 or more, a fatty acid(s) with a carbon number of 20 or more and a double bond number of 4 or more, or a fatty acid(s) with a carbon number of 20 or more and a double bond number of 5 or more. Specific examples include α-linoleic acid (18:3, n-3), γ-linoleic acid (18:3, n-6), arachidonic acid (20:4, n-6), dihomo-γ-linoleic acid (20:3, n-6), eicosapentaenoic acid (20:5, n-3), docosapentaenoic acid (22:5, n-6), docosahexaenoic acid (22:6, n-3), etc. In a preferred embodiment, the at least one highly unsaturated fatty acid is n-3 highly unsaturated fatty acids, and more preferably eicosapentaenoic acid and/or docosahexaenoic acid.

Glycerides containing at least one highly unsaturated fatty acid as a constituent fatty acid are known to be abundant in certain kinds of microorganism oils, vegetable oils, and marine animal oils. Specific examples include: fish oils such as sardine oil, tuna oil, bonito oil, menhaden oil, cod liver oil, herring oil, capelin oil, and salmon oil; marine animal oils as from crustaceans such as krill; vegetable oils as from *perilla*, flax, soybean, and rapeseed; fats or oils produced by microorganisms belonging to the genus *Mortierella*, the genus *Penicillium*, the genus *Aspergillus*, the genus *Rhodotorula*, and the genus *Fusarium*. In one embodiment, the at least one highly unsaturated fatty acid, salt thereof, and ester thereof according to the present invention are those which derives from the above-mentioned fats or oils. These fats or oils may be purified or concentrated oils as manufactured in accordance with the usual manner. Free highly unsaturated fatty acids, salts and non-glyceride esters thereof can be prepared by methods known to persons skilled in the art, starting, for example, from the above-mentioned glyceride.

The salt of the at least one highly unsaturated fatty acid to be used in the present invention is exemplified by potassium salts and sodium salts. The ester of the at least one highly unsaturated fatty acid is exemplified by esters of lower alcohols with a carbon number of 5 or less (such as methyl ester, ethyl ester, n-propyl ester, i-propyl ester, n-butyl ester, s-butyl ester, t-butyl ester, and n-pentyl ester), esters with glycerin such as monoglyceride, diglyceride and triglyceride (i.e., collectively referred to as glycerides), and phospholipids, with glycerides being preferred.

In one embodiment, the at least one highly unsaturated fatty acid in the composition of the present invention accounts for 10-70 wt %, say, 15-50 wt % or 20-40 wt %, of constituent fatty acids. In a preferred embodiment where the at least one highly unsaturated fatty acid is EPA and DHA, the at least one highly unsaturated fatty acid in the composition of the present invention accounts for 5-65 wt %, say, 10-45 wt % or 15-35 wt %, of constituent fatty acids.

As used herein, the proportion of specific fatty acids (wt %) relative to all fatty acids in the composition is calculated, unless otherwise noted, on the basis of the values of measurement by gas chromatography following esterification of components in the composition in accordance with "AOCS official method Celb-89." The content of fatty acids, as referred to herein, also means the above-mentioned proportion of specific fatty acids (wt %) relative to all fatty acids in the composition. Analytical conditions of gas chromatography are as follows.

Apparatus: Agilent 6890N GC system (Agilent Technologies, Inc.)
Column: DB-WAX (Agilent Technologies, 30 m×0.25 mm ID, 0.25 µm film thickness)
Carrier gas: helium (1.0 mL/min, constant flow)
Injection port temperature: 250° C.
Injection volume: 1 µL
Injection method: split
Split ratio: 20:1
Column oven: 180° C.-3° C./min-230° C.
Detector: FID
Detector temperature: 250° C.

In one embodiment, the composition of the present invention further contains a component selected from at least one middle chain fatty acid, salt thereof, and ester thereof as an active ingredient. The at least one middle chain fatty acid to be used in the present invention is one with a carbon number of 8-12 and it may be either saturated or unsaturated. Specific examples include caprylic acid, pelargonic acid, capric acid, lauric acid, and so on. The at least one middle chain fatty acid may be either a single middle chain fatty acid or a combination of two or more middle chain fatty acids. In a preferred embodiment, the at least one middle chain fatty acid is caprylic acid and/or capric acid. Glycerides having at least one middle chain fatty acid as a constituent fatty acid are known to be abundant in coconut oil, palm oil, and the like. In one embodiment, the at least one middle chain fatty acid, salt thereof, and ester thereof to be used in the present invention are those which derives from the above-mentioned fats or oils. These fats or oils may be purified or concentrated oils that are manufactured in accordance with the usual manner. Free middle chain fatty acids, salts and non-glyceride esters thereof can be prepared by known methods, starting, for example, from the glycerides contained in the above-mentioned fats or oils. In the composition of the present invention, a middle chain fatty acid triglyceride of high purity as prepared by purifying at least one free middle chain fatty acid and subjecting the purified free middle chain fatty acid to esterification reaction with glycerin may be contained as an active ingredient.

In one embodiment, the at least one highly unsaturated fatty acid in the composition of the present invention accounts for 10-70 wt %, say, 15-50 wt % or 20-40 wt %, of constituent fatty acids and the at least one middle chain fatty acid in the composition accounts for 20-70 wt %, say, 30-60 wt % or 40-55 wt %, of constituent fatty acids. In one embodiment where the at least one highly unsaturated fatty acid is EPA and DHA and the at least one middle chain fatty acid is caprylic acid and capric acid, the at least one highly unsaturated fatty acid in the composition of the present invention accounts for 5-65 wt %, say, 10-45 wt % or 15-35 wt %, of constituent fatty acids and the at least one middle chain fatty acid in the composition accounts for 20-70 wt %, say, 30-60 wt % or 40-55 wt %, of constituent fatty acids.

In one embodiment, the active ingredients in the composition of the present invention are a triglyceride comprising the at least one highly unsaturated fatty acid as a constituent fatty acid and a triglyceride comprising the at least one middle chain fatty acid as a constituent fatty acid.

The triglyceride containing the at least one highly unsaturated fatty acid as a constituent fatty acid is exemplified by one which derives, for example, from fish oils and marine animal oils as from crustaceans such as krill, vegetable oils as from *perilla*, flax, soybean, and rapeseed, fats or oils produced by microorganisms belonging to the genus *Mortierella*, the genus *Penicillium*, the genus *Aspergillus*, the genus *Rhodotorula*, and the genus *Fusarium*.

The triglyceride comprising the at least one middle chain fatty acid as a constituent fatty acid is exemplified by one which derives, for example, from coconut oil, palm oil, and the like. As regards the triglyceride comprising the at least one middle chain fatty acid as a constituent fatty acid, the proportion of the at least one middle chain fatty acid in constituent fatty acids can be 90 wt % or more, 95 wt % or more, 97 wt % or more, 99 wt % or more, or even 100 wt %. In a preferred embodiment, the triglyceride comprising the at least one middle chain fatty acid as a constituent fatty acid is a triglyceride comprising only middle chain fatty acids as constituent fatty acids (MCT).

In one embodiment, the active ingredient in the composition of the present invention is a mixed oil consisting of a triglyceride comprising the at least one highly unsaturated fatty acid as a constituent fatty acid and a triglyceride comprising the at least one middle chain fatty acid as a constituent fatty acid. In a preferred embodiment, the triglyceride comprising the at least one middle chain fatty acid as a constituent fatty acid is a triglyceride comprising only middle chain fatty acids as constituent fatty acids (MCT). As will be described in the Examples to be given later in this specification, a mixed oil consisting of the triglyceride comprising the at least one highly unsaturated fatty acid as a constituent fatty acid and the triglyceride comprising the at least one middle chain fatty acid as a constituent fatty acid has a lymphatic circulation improving effect.

Such mixed oil can be prepared by, for example, physically mixing the triglyceride comprising the at least one highly unsaturated fatty acid as a constituent fatty acid with the triglyceride comprising the at least one middle chain fatty acid as a constituent fatty acid. The mixing ratio may be appropriately set so that the lymphatic circulation improving effect is obtained, for example, in such a way that the proportion of each of the at least one highly unsaturated fatty acid and the at least one middle chain fatty acid in the composition of the present invention will assume the value indicated above.

In a preferred embodiment, the active ingredient in the composition of the present invention is a triglyceride comprising the at least one highly unsaturated fatty acid and the at least one middle chain fatty acid as constituent fatty acids in one molecule. As will be described in the Examples to be given later in this specification, the triglyceride comprising the at least one highly unsaturated fatty acid and the at least one middle chain fatty acid as constituent fatty acids in one molecule has the lymphatic circulation improving effect further enhanced in comparison with the mixed oil that is identical in terms of fatty acid composition.

In order to prepare such triglyceride, the aforementioned triglyceride comprising the at least one highly unsaturated fatty acid as a constituent fatty acid and the triglyceride comprising the at least one middle chain fatty acid as a constituent fatty acid may, for example, be subjected to transesterification. The catalyst to be used in ester interchange may be a chemical catalyst or an enzyme (lipase). In ester interchange using a chemical catalyst, the constituent fatty acids will be bonded at random positions. Note that triglycerides of this type that have been prepared from naturally occurring triglycerides by modifying the positions at which the constituent fatty acids are bonded and modifying fatty acid composition are sometimes referred to as structured lipids.

In the case of using a chemical catalyst, about 0.1-2 wt % of the catalyst may first be added to the mixed oil consisting of the triglyceride comprising the at least one highly unsaturated fatty acid as a constituent fatty acid and the triglyceride comprising the at least one middle chain fatty acid as a constituent fatty acid, and the resulting mixture is subjected to reaction under stirring at an atmospheric or reduced pressure for 3-120 minutes at 50-270° C. By performing ordinary purification steps such as washing with water, drying, decoloring, and deodorizing, the end product can be obtained. The ratio at which the triglyceride comprising the at least one highly unsaturated fatty acid as a constituent fatty acid is mixed with the triglyceride comprising the at least one middle chain fatty acid as a constituent fatty acid may be set appropriately so that the lymphatic circulation improving effect is obtained, for example, in such a way that the proportion of each of the at least one highly unsaturated fatty acid and the at least one middle chain fatty acid in the composition of the present invention will assume the value indicated above.

The applicable chemical catalyst may be exemplified by alkali metal hydroxides such as lithium hydroxide, sodium hydroxide and potassium hydroxide, or alkali metal alkoxides such as lithium methoxide and sodium methoxide.

Having the lymphatic circulation improving effect, the composition of the present invention can be used for ameliorating edema, ameliorating swollenness, ameliorating excessive sensitivity to cold, ameliorating skin roughness, ameliorating skin dullness, reducing cellulites and body fat, mitigating stress, detoxing (excreting wastes out of the body), or ameliorating disorders due to exercise. In one embodiment, the composition of the present invention is used for ameliorating edema such as lymphedema that results from a stagnation of the lymph flow.

The composition of the present invention is to be administered to mammals, preferably a human. In one embodiment, the composition of the present invention is administered to subjects having symptoms of edema (e.g. lymphedema), excessive sensitivity to cold, skin roughness or skin dullness, subjects having cellulites, subjects having stress, subjects who need detoxing, or subjects having disorders due to exercise, and these symptoms can be ameliorated by improving the lymphatic circulation in those subjects.

The composition of the present invention may be prepared in forms suitable for pharmaceutical compositions, food compositions (e.g. functional foods, health foods, and supplements), food additives, and the like, as exemplified by various solid preparations including granules (including dry syrups), capsules (soft capsules and hard capsules), tablets (including chewables), powders and pills, as well as liquid preparations including liquids for internal application (including liquids, suspensions, and syrups). For instance, the composition of the present invention can be formulated as soft capsules that have the active ingredient filled into a gelatin shell.

Additives for formulation include, for example, excipients, lubricants, binders, disintegrants, fluidizers, dispersants, wetting agents, preservatives, viscous agents, pH modifiers, coloring agents, flavoring agents, surfactants, and solubilizers. If liquids are to be formulated, thickeners can be incorporated, as exemplified by pectin, xanthan gum, and guar gum. In other cases, coating agents may be used to formulate coated tablets; alternatively, pasty leim may be formulated. Even in the case of preparing other forms, conventional methods may be followed.

The composition of the present invention can assume the form of food compositions or food additives. As used herein, the term "food compositions" refers to foods in general that include beverages; it encompasses not only common foods including health foods such as supplements but also foods for specified health uses (FOSHU) and foods with nutrient function claims (FNFC), both being specified in the Consumer Affairs Agency's System of Foods with Health Claims. For instance, there are provided functional foods labeled with the indication to the effect that they have a lymphatic circulation improving effect. In one exemplary case, fish oil containing foods may be provided as such. In another exemplary case, the food composition or food additive of the present invention also encompasses food ingredients for imparting the lymphatic circulation improving effect as by being added to, mixed with or coated on other foods. For use other than as foods, the food composition or food additive of the present invention may be provided as animal feeds or the like.

The food composition or food additive of the present invention can be prepared by incorporating the composition of the present invention into a food composition or a food additive, whereupon the lymphatic circulation improving function is imparted.

The food composition of the present invention may be beverages, confectionery, bread, soup, etc. and may be exemplified by common retorted foods, frozen foods, instant foods (e.g. instant noodles), canned foods, sausages, cookies, biscuits, cereal bars, crackers, snacks (e.g. potato chips), pastry, cakes, pies, candies, chewing gum (including pellets and sticks), jellies, soup, ice cream, dressings, yoghurt, etc.; supplements in such forms as tablet, capsule, and emulsion; and refreshing beverages. Methods of producing these foods are not particularly limited as long as they do not impair the effects of the present invention, and methods employed for respective foods by persons skilled in the art may be followed.

Selling the products according to the present invention with their packaging containers, product manuals or brochures indicating the effects to be exhibited by the composition of the present invention is included within the scope of the present invention. Advertising and selling the products according to the present invention with their effects displayed on TV or indicated on the internet's web sites, brochures, newspapers, magazines, etc. are also included within the scope of the present invention.

The amount of the active ingredient to be ingested by subjects in the present invention is not particularly limited and it may, for example, be ingested in amounts no less than the effective amount for obtaining the desired effects. As used herein, the term "the effective amount for obtaining the desired effects" refers to the amount necessary for improving lymphatic circulation. In the case of an adult, for example, the active ingredient may be ingested in no less than 20 mg/kg body weight/day, say, no less than 50 mg/kg body/day or no less than 100 mg/kg body/day, depending on various conditions such as the age, body weight and health status of the subject. Since the active ingredient in the composition of the present invention does not have strong side effects, its daily intake is not limited in any way but 500 mg/kg body/day and less may be given as an example.

EXAMPLES

On the following pages, the present invention will be further described by means of the Examples but they are by no means intended to limit the scope of the present invention.

In the Examples given below, indications of percentage refer to % by weight unless otherwise noted.

Example 1

[Materials and Methods]
<Preparation of Triglycerides>

A purified fish oil (product of Nippon Suisan Kaisha, Ltd., with specified values of 28 wt % EPA and 12 wt % DHA) and a triglyceride having only middle chain fatty acids as constituent fatty acids (MCT; ca 60 wt % caprylic acid and ca 40 wt % capric acid) were used. The purified fish oil and MCT were mixed at a weight ratio of 55:45 and after adding 0.2 wt % of sodium methoxide, the mixture was stirred at 60-80° C. for 60 minutes to effect ester interchange. The resulting product was washed with water, dried, decolored and deodorized to prepare a triglyceride the constituent fatty acids of which were the fatty acids derived from the EPA containing fish oil and the middle chain fatty acids (the triglyceride is hereunder referred to as STG).

A mixed oil was prepared as a control sample by mixing the purified fish oil and MCT at a weight ratio of 50:50 (the mixed oil is hereunder referred to as PM).

<Feed's Composition>

In accordance with the composition of American Institute of Nutrition (AIN)-93G, a feed (training diet) comprising 7% of soybean oil as a feed fat was prepared and fed to rats during two periods, one being before a surgery for thoracic duct lymph cannulation and one being a recuperative period after the surgery for thoracic duct lymph cannulation. As the experimental diets to be given during lymph collection, the following two were prepared: a feed which, according to AIN-93G, contained 10% of eicosapentaenoic acid (EPA)/middle chain fatty acid (MCFA) structured lipid (STG) and 0.2% of cholesterol (this feed is referred to as STG diet); a feed containing 10% of a mixed fat or oil prepared by physically mixing the EPA-containing fish oil and MCFA triacylglycerol (MCT) in such a way that it would be identical to STG in terms of fatty acid composition (the mixed fat or oil is hereunder referred to as PM), plus 0.2% of cholesterol (this feed is referred to as PM diet). The composition of the respective feeds is shown in Table 1. Fatty acid composition in STG and PM is shown in Table 2.

TABLE 1

Composition of Experimental Diet

| Component (g/kg diet) | Training diet | PM diet | STG diet |
| --- | --- | --- | --- |
| Corn starch | 397.486 | 365.486 | 365.486 |
| Casein | 200 | 200 | 200 |
| Dextrinized corn starch | 132 | 132 | 132 |
| Sucrose | 100 | 100 | 100 |
| Soybean oil | 70 | — | — |
| Physical mix (PM)*[1] | — | 100 | — |
| Structured triacylglycerols (STG)*[1] | — | — | 100 |
| Cellulose | 50 | 50 | 50 |
| Mineral mix (AIN-93G-MX) | 35 | 35 | 35 |
| Vitamin mix (AIN-93VX) | 10 | 10 | 10 |
| L-cystine | 3 | 3 | 3 |
| Choline bitartrate | 2.5 | 2.5 | 2.5 |
| Cholesterol | — | 2 | 2 |
| TBHQ | 0.014 | 0.014 | 0.014 |

*[1]PM and STG were prepared by the methods described in the text.

TABLE 2

Fatty Acid Composition of the Oils Used in the Experiment

| | MCT | Fish oil (wt %) | PM | STG |
| --- | --- | --- | --- | --- |
| C8:0 | 57.9 | — | 28.9 | 28.9 |
| C10:0 | 42.1 | — | 21 | 21.4 |
| C12:0 | 0.1 | 0.1 | 0.1 | 0.1 |
| C14:0 | — | 6.1 | 3 | 3.1 |
| C15:0 | — | 0.3 | 0.2 | 0.2 |
| C16:0 | — | 7.7 | 3.9 | 2.7 |
| C16:1n-7 | — | 9.9 | 4.9 | 5 |
| C17:0 | — | 0.2 | 0.1 | 0.1 |
| C18:0 | — | 0.6 | 0.3 | 0.3 |
| C18:1t | — | 0.1 | — | 0.1 |
| C18:1c | — | 4.3 | 2.2 | 2.7 |
| C18:2n-6 | — | — | — | 0.1 |
| C18:3n-6 | — | 0.3 | 0.2 | 0.2 |
| C20:1 | — | 0.6 | 0.3 | 0.3 |
| C20:2n-6 | — | 0.6 | 0.3 | 0.3 |
| C20:3n-6 | — | 0.1 | 0.1 | 0.1 |
| C20:3n-3 | — | 0.1 | — | — |
| C20:4n-6 | — | 1.2 | 0.6 | 0.6 |
| C20:5n-3 | — | 30.9 | 15.5 | 15.5 |
| C22:1 | — | 0.1 | — | — |
| C22:2 | — | 1 | 0.5 | 0.5 |
| C22:5n-3 | — | 2.8 | 1.4 | 1.4 |
| C22:6n-3 | — | 12.5 | 6.3 | 6.4 |
| C24:1 | — | 0.1 | — | 0.1 |
| Others | — | 20.6 | 10.5 | 10.1 |
| Total | 100 | 100 | 100 | 100 |

—: Not detected.

<Conditions for Rearing Laboratory Animals>

In the experiment, 7-wk old male (weighing 230-240 g) Sprague-Dawley (Kud:SD) rats (KYUDO COMPANY, Tosu) were used and reared at room temperature (21-23° C.) with a lighting cycle of 12 hours (turned on at 8:00 and turned off at 20:00). The feeding method was based on the meal-feeding approach, in which the animals were fed the meal for a total of 2 hours (one hour in the morning from 10:00 to 11:00 and one hour in the evening from 16:00 to 17:00) while drinking water ad libitum. The rearing schedule is shown in FIG. 1. After 5-day rearing on the training diet, the animals were given a surgery for semi-permanent cannulation of thoracic duct lymph under inhalation anesthesia with isoflurane. The surgery was followed by a 2-day recuperative period, during which the training diet was also given as per the schedule described above. On the 3$^{rd}$ post-operative day, the animals were fed the STG diet or PM diet for 30 minutes (n=6/group). From both the STG diet group and PM diet group, lymph was collected for 20 minutes before the feeding and for 7 hours since the start of the feeding (BHT was added in order to prevent lipid oxidation). After lymph collection, the laboratory animals were sacrificed by drawing blood from an abdominal aorta under anesthesia with the combination of SOMNOPENTYL® (KYORITSU SEIYAKU CORPORATION, Tokyo) and isoflurane; the mucosa of the upper small intestine and blood serum were then obtained (and stored at −30° C. until analysis).

<Surgery for Semi-Permanent Cannulation of Thoracic Duct Lymph>

SD rats were subjected to inhalation anesthesia with isoflurane, during which a SILASCON® medical tube (KANEKA MEDICAL PRODUCTS, Tokyo) filled with heparin in physiological saline was inserted into a lymphatic vessel in the thoracic duct. The tube was fixed and sutured to the endothelium and thereafter fixed to the head by a subcutaneous route. To assure the prevention of post-operative infection, an appropriate amount of a sulfamethoxazole powder (nacalai tesque, Kyoto) was applied to the laparotomy-affected area, and to assure post-operative pain control, the analgesic Betorfal (Meiji Seika Pharma Co., Ltd., Tokyo) was administered intraperitoneally. In addition, to restore strength, an isotonic aqueous solution containing 139 mM glucose and 85 mM sodium chloride was given as drinking water.

<Measurement of Lymph Flow Rate>

The flow rate of the lymph collected for 20 minutes before feeding of the experimental diet was converted to a value per hour, which was designated as the 0-hour value; the lymph flow rate from the start of feeding to an hour after feeding was designated as the value for the first hour.

The same procedure was repeated until the value for the seventh hour was obtained.

[Results]

<Effects of the Structured Lipid on the Lymph Flow Rate]

Figure 2:
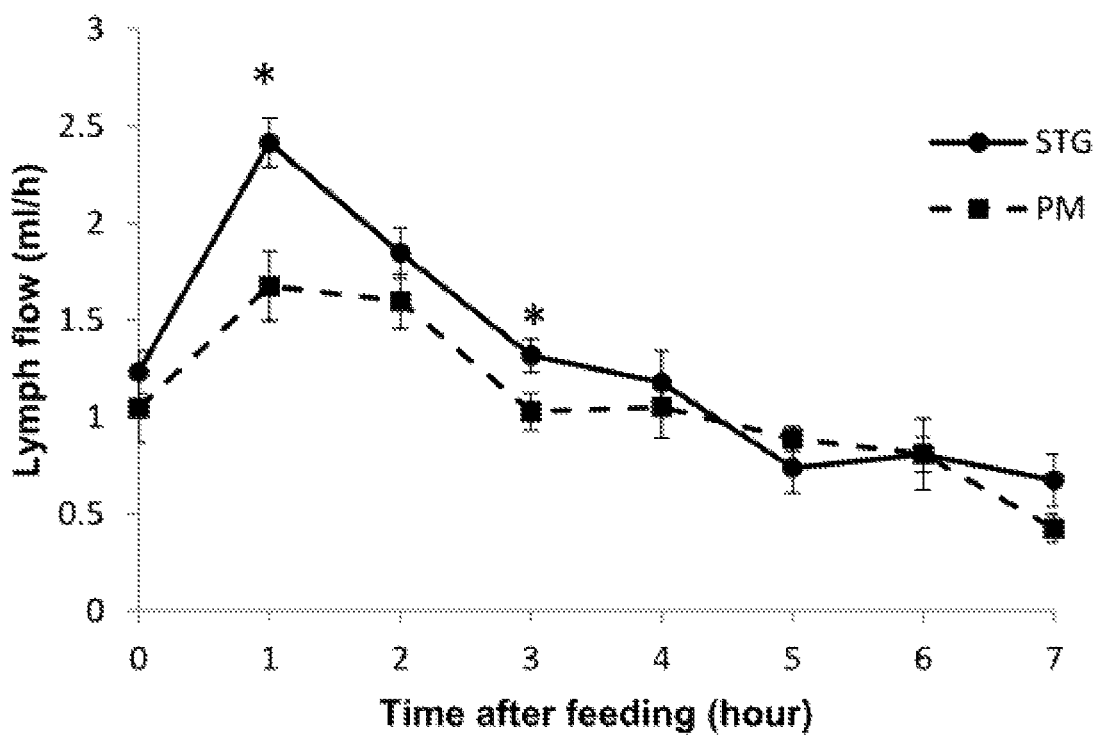
FIG. 2 is a graph showing hourly changes in the lymph flow rate (mL/h) in STG and PM groups. *: p<0.05.

In both the PM group and STG group, the lymph flow increased immediately after the feeding. It should be noted that, when the feed containing no highly unsaturated fatty acids was ingested, no increase in the lymph flow rate was confirmed. In addition, the lymph flow rates at the first and third hours after the intake of STG increased significantly as compared with the values from the PM group (FIG. 2 and Table 3). It was therefore shown that highly unsaturated fatty acids have an action for increasing the lymph flow rate and that the lymphatic circulation improving effect is further enhanced by formulating a triglyceride comprising highly unsaturated fatty acids and middle chain fatty acids as constituent fatty acids.

TABLE 3

Hourly Lymph Flow Rates in STG and PM

| | Hourly Lymph Flow Rate (ml/hour) | | | | | | | |
|---|---|---|---|---|---|---|---|---|
| | 0 h | 1 h | 2 h | 3 h | 4 h | 5 h | 6 h | 7 h |
| EPA/MCT structured lipid (STG) | 1.23 | 2.42 | 1.85 | 1.32 | 1.18 | 0.74 | 0.81 | 0.67 |
| SE | 0.11 | 0.13 | 0.13 | 0.09 | 0.16 | 0.13 | 0.09 | 0.14 |
| EPA/MCT mixed oil (PM) | 1.05 | 1.68 | 1.60 | 1.03 | 1.05 | 0.89 | 0.81 | 0.43 |
| SE | 0.18 | 0.18 | 0.14 | 0.10 | 0.16 | 0.06 | 0.18 | 0.07 |

Example 2

[Materials and Methods]
<Feed's Composition>

In accordance with the composition of American Institute of Nutrition (AIN)-93G, a feed (training diet) comprising 7% of soybean oil as a feed fat was prepared and fed to rats during two periods, one being before a surgery for thoracic duct lymph cannulation and one being a recuperative period after the surgery for thoracic duct lymph cannulation. As the experimental diet to be given during lymph collection, a feed comprising 10% of a fish oil containing EPA and other highly unsaturated fatty acids with carbon numbers of 20 and more (i.e., fish oil diet) was prepared in accordance with AIN-93G. In addition, as an experimental diet that was free of EPA, DHA and other highly unsaturated fatty acids with carbon numbers of 20 and more, a feed comprising 10% of soybean oil (i.e., soybean oil diet) was prepared in accordance with AIN-93G. The composition of the respective feeds is shown in Table 4. Fatty acid composition in the soybean oil and the fish oil is shown in Table 5.

TABLE 4

Composition of Experimental Diet

| Component (g/kg diet) | Training diet | Soybean oil diet | Fish oil diet |
|---|---|---|---|
| Corn starch | 397.486 | 367.486 | 367.486 |
| Casein | 200 | 200 | 200 |
| Dextrinized corn starch | 132 | 132 | 132 |
| Sucrose | 100 | 100 | 100 |
| Soybean oil | 70 | 100 | — |
| Fish oil | — | — | 100 |
| Cellulose | 50 | 50 | 50 |
| Mineral mix (AIN-93G-MX) | 35 | 35 | 35 |
| Vitamin mix (AIN-93VX) | 10 | 10 | 10 |
| L-cystine | 3 | 3 | 3 |
| Choline bitartrate | 2.5 | 2.5 | 2.5 |
| TBHQ | 0.014 | 0.014 | 0.014 |

TABLE 5

Fatty Acid Composition of the Oils Used in the Experiment

| | Soybean oil | Fish oil |
|---|---|---|
| | (wt %) | |
| C8:0 | — | — |
| C10:0 | — | — |
| C12:0 | — | 0.1 |
| C14:0 | — | 6.1 |
| C15:0 | — | 0.3 |
| C16:0 | 12.4 | 7.7 |

TABLE 5-continued

Fatty Acid Composition of the Oils Used in the Experiment

|  | Soybean oil (wt %) | Fish oil |
|---|---|---|
| C16:1n-7 | 0.2 | 9.9 |
| C17:0 | 0.1 | 0.2 |
| C18:0 | 6.6 | 0.6 |
| C18:1t | 0.2 | 0.1 |
| C18:1c | 25.7 | 4.3 |
| C18:2n-6 | 42.1 | — |
| C18:3n-6 | — | 0.3 |
| C18:3n-3 | 7.3 | — |
| C20:1 | — | 0.6 |
| C20:2n-6 | — | 0.6 |
| C20:3n-6 | — | 0.1 |
| C20:3n-3 | — | 0.1 |
| C20:4n-6 | — | 1.2 |
| C20:5n-3 | — | 30.9 |
| C22:1 | — | 0.1 |
| C22:2 | — | 1.0 |
| C22:5n-3 | — | 2.8 |
| C22:6n-3 | — | 12.5 |
| C24:1 | — | 0.1 |
| Others | 5.5 | 20.6 |
| Total | 100 | 100 |

—: Not detected.

<Conditions for Rearing Laboratory Animals>

In the experiment, 10-wk old male (weighing 330-380 g) Sprague-Dawley (Jcl:SD) rats (KYUDO COMPANY, Tosu) were used and reared at room temperature (21-23° C.) with a lighting cycle of 12 hours (turned on at 8:00 and turned off at 20:00). The feeding method was based on the meal-feeding approach, in which the animals were fed for a total of 2 hours (one hour in the morning from 10:00 to 11:00 and one hour in the evening from 16:00 to 17:00) while drinking water ad libitum. After 5-day rearing on the training diet, the animals were given a surgery for semi-permanent cannulation of thoracic duct lymph under inhalation anesthesia with isoflurane. The surgery was followed by a 2-day recuperative period, during which the training diet was given as per the schedule described above. On the $3^{rd}$ post-operative day, the animals were fed the soybean oil diet or fish oil diet for 30 minutes (n=2/group). From both the soybean oil diet group and fish oil diet group, lymph was collected for 20 minutes before the feeding and for 7 hours since the start of the feeding (BHT was added in order to prevent lipid oxidation).

<Surgery for Semi-Permanent Cannulation of Thoracic Duct Lymph>

SD rats were subjected to inhalation anesthesia with isoflurane, during which a SILASCON® medical tube (KANEKA MEDICAL PRODUCTS, Tokyo) filled with heparin in physiological saline was inserted into a lymphatic vessel in the thoracic duct. The tube was fixed and sutured to the endothelium and thereafter fixed to the head by a subcutaneous route. To ensure prevention of post-operative infection, an appropriate amount of a sulfamethoxazole powder (nacalai tesque, Kyoto) was applied to the laparotomy-affected area, and to ensure post-operative pain control, the analgesic Betorfal (Meiji Seika Pharma Co., Ltd., Tokyo) was administered intraperitoneally. In addition, to restore strength, an isotonic aqueous solution containing 139 mM glucose and 85 mM sodium chloride was given as drinking water.

<Measurement of Lymph Flow Rate>

The flow rate of the lymph collected for 20 minutes before feeding of the experimental diet was converted to a value per hour, which was designated as the 0-hour value; the lymph flow rate from the start of feeding to an hour after feeding was designated as the value for the first hour.

The same procedure was repeated until the value for the seventh hour was obtained.

[Results]

<Effects of Fish Oil Ingestion on the Lymph Flow Rate]

Figure 3:
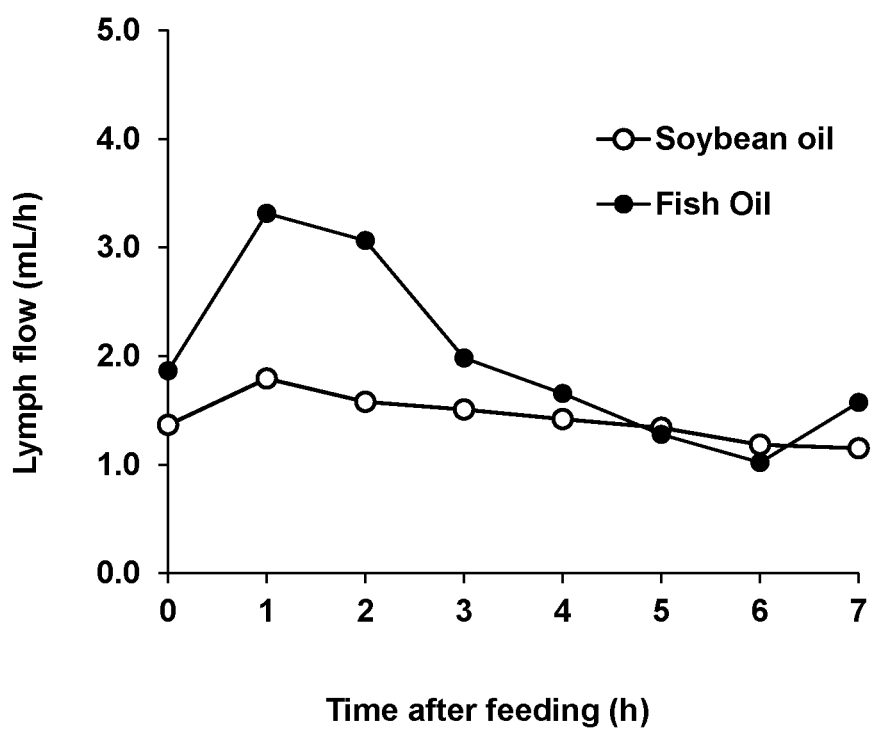
FIG. 3 is a graph showing hourly changes in the lymph flow rate (mL/h) in Fish oil and Soybean oil groups.

In the soybean oil group, the lymph flow rate increased only slightly after the feeding. On the other hand, in the fish oil group, a considerable increase in the lymph flow rate was observed at the first hour after ingestion (FIG. 3). It was thus shown that EPA, DHA and other highly unsaturated fatty acids with carbon numbers of 20 and more have an action for increasing the lymph flow rate.

INDUSTRIAL APPLICABILITY

According to the present invention, food compositions, food additives and the like that improve lymphatic circulation are provided. According to the present invention, food compositions, food additives and the like that can be used for ameliorating edema, ameliorating excessive sensitivity to cold, ameliorating skin roughness, ameliorating skin dullness, reducing cellulites and body fat, mitigating stress, detoxing (excreting wastes out of the body), or ameliorating disorders due to exercise are also provided.

The invention claimed is:

1. A method of improving lymphatic circulation for ameliorating edema, ameliorating excessive sensitivity to cold, ameliorating skin roughness, ameliorating skin dullness, mitigating stress, excreting wastes out of the body, or ameliorating disorders due to exercise, which comprises allowing a subject in need thereof to ingest an effective amount of a composition which contains a component selected from at least one highly unsaturated fatty acid, salt thereof, and ester thereof as an active ingredient, wherein the at least one highly unsaturated fatty acid is eicosapentaenoic acid or docosahexaenoic acid.

2. The method as recited in claim 1, wherein the composition further contains a component selected from at least one middle chain fatty acid, salt thereof, and ester thereof as an active ingredient.

3. The method as recited in claim 2, wherein the active ingredients are a triglyceride comprising the at least one highly unsaturated fatty acid as a constituent fatty acid and a triglyceride comprising the at least one middle chain fatty acid as a constituent fatty acid.

4. The method as recited in claim 2, wherein the active ingredient is a triglyceride comprising the at least one highly unsaturated fatty acid and the at least one middle chain fatty acid as constituent fatty acids.

5. The method as recited in claim 2, wherein the at least one highly unsaturated fatty acid in the composition accounts for 10-70 wt % of constituent fatty acids and the at least one middle chain fatty acid in the composition accounts for 20-70 wt % of constituent fatty acids.

6. The method as recited in claim 1, wherein the composition is in the form of a food composition or a food additive.

* * * * *